(12) United States Patent
Wiesner et al.

(10) Patent No.: US 7,731,138 B2
(45) Date of Patent: Jun. 8, 2010

(54) FLEXIBLE CLAMPING APPARATUS FOR MEDICAL DEVICES

(75) Inventors: Joel Wiesner, St. Peters, MO (US); Rick A. Sisk, Washington, MO (US)

(73) Assignee: Covidien AG (CH)

( * ) Notice: Subject to any disclaimer, the term of this patent is extended or adjusted under 35 U.S.C. 154(b) by 913 days.

(21) Appl. No.: 11/138,200

(22) Filed: May 26, 2005

(65) Prior Publication Data
US 2006/0278785 A1    Dec. 14, 2006

(51) Int. Cl.
*F16M 13/00* (2006.01)
(52) U.S. Cl. .............. 248/160; 248/230.6; 248/231.71
(58) Field of Classification Search ................. 248/160, 248/231.71, 230.6, 229.15
See application file for complete search history.

(56) References Cited

U.S. PATENT DOCUMENTS

| | | |
|---|---|---|
| 184,957 A | 12/1876 | Doeg |
| 252,969 A | 1/1882 | Porter |
| 291,248 A | 1/1884 | West |
| 989,893 A | 4/1911 | Brick |
| 1,059,217 A | 4/1913 | Rudy |
| 1,066,357 A | 7/1913 | Yardley |
| 1,160,103 A | 11/1915 | Burkhart |
| 1,403,863 A | 1/1922 | Peat |
| 1,749,491 A | 3/1930 | Kokay |
| 2,101,317 A | 12/1937 | Lemieux |
| 2,116,263 A | 5/1938 | Harbaugh |
| 2,322,107 A | 6/1943 | Balcar |
| 2,448,402 A | 8/1948 | Thompson |
| 2,638,301 A | 5/1953 | Smith |
| 2,756,789 A | 7/1956 | Kraus et al. |
| 2,867,003 A | 1/1959 | Stiles |
| 2,945,946 A | 7/1960 | Moffatt |
| 3,268,853 A | 8/1966 | Noker et al. |
| 3,442,478 A | 5/1969 | Parapetti |
| 3,803,012 A | 4/1974 | Kurr |
| 3,883,128 A | 5/1975 | Breese |
| 4,164,344 A | 8/1979 | Deragne |
| 4,262,872 A | 4/1981 | Kodet |
| 4,365,792 A | 12/1982 | Johns |
| 4,432,538 A | 2/1984 | Sequin |
| 4,443,128 A | 4/1984 | Yamamoto |
| 4,487,523 A | 12/1984 | Monroe |
| 4,500,077 A | 2/1985 | Coxon |

(Continued)

FOREIGN PATENT DOCUMENTS

EP    0 167 345 A    1/1986

*Primary Examiner*—Gwendolyn Baxter
(74) *Attorney, Agent, or Firm*—Edward S. Jarmolowicz, Esq.

(57) ABSTRACT

A mounting apparatus of the present invention is used in a medical environment to releasably secure a device to a support member. The mounting apparatus has a flexible shaft with a first end for releasable attachment to the support member and a second end for releasable attachment to the device. A generally C-shaped clamping member at the first end releasably attaches the apparatus to the support member. The clamping member has an inner surface, an outer surface, and at least two apertures including a first aperture through which a securing rod passes and a second aperture for releasable attachment of the flexible shaft. The present invention is also directed to a powered medical device assembly having a medical device and a flexible shaft capable of selective mounting of the medical device on a support.

8 Claims, 15 Drawing Sheets

U.S. PATENT DOCUMENTS

| | | |
|---|---|---|
| 4,504,046 A | 3/1985 | Yonezawa et al. |
| 4,547,092 A | 10/1985 | Vetter |
| 4,560,152 A | 12/1985 | Miller |
| 4,576,501 A | 3/1986 | McConnell |
| 4,676,687 A | 6/1987 | Koffler |
| 4,695,025 A | 9/1987 | Vaughan |
| 4,697,800 A | 10/1987 | Stahl et al. |
| 4,699,344 A | 10/1987 | Vaughan |
| 4,702,448 A | 10/1987 | LoJacono |
| 4,706,368 A | 11/1987 | Crissman, III et al. |
| 4,742,981 A | 5/1988 | Converse |
| 4,747,590 A * | 5/1988 | Yang .......................... 269/45 |
| 4,796,846 A | 1/1989 | Meier |
| 4,832,294 A | 5/1989 | Eidem |
| 4,832,299 A | 5/1989 | Gorton et al. |
| 4,842,174 A * | 6/1989 | Sheppard et al. ............ 224/548 |
| 4,850,099 A | 7/1989 | Scollard |
| 4,852,841 A | 8/1989 | Sebring |
| 4,865,484 A | 9/1989 | McConnell |
| 4,881,843 A | 11/1989 | Randleman |
| 4,885,667 A | 12/1989 | Selden |
| 4,957,021 A | 9/1990 | Helton |
| 4,958,873 A | 9/1990 | Akagawa |
| 4,969,768 A | 11/1990 | Young |
| 4,982,988 A | 1/1991 | Murphy |
| 5,025,780 A | 6/1991 | Farley |
| 5,108,213 A | 4/1992 | Shields |
| 5,118,127 A | 6/1992 | Partington |
| 5,139,359 A | 8/1992 | Rakar et al. |
| 5,161,787 A | 11/1992 | Hobday |
| 5,163,752 A | 11/1992 | Copeland et al. |
| 5,174,533 A | 12/1992 | Pryor et al. |
| 5,197,360 A | 3/1993 | Wooster, Jr. |
| 5,226,638 A | 7/1993 | Ausilio |
| 5,236,213 A | 8/1993 | Trickett |
| 5,242,240 A | 9/1993 | Gorham |
| 5,246,217 A | 9/1993 | Brot |
| 5,312,094 A | 5/1994 | Zera |
| 5,314,175 A | 5/1994 | Izumi et al. |
| 5,320,444 A | 6/1994 | Bookwalter |
| 5,326,059 A | 7/1994 | Pryor et al. |
| 5,332,184 A | 7/1994 | Davis |
| 5,342,011 A | 8/1994 | Short |
| 5,346,194 A | 9/1994 | Coffin, III |
| 5,385,324 A | 1/1995 | Pryor et al. |
| 5,415,383 A | 5/1995 | Ausilio |
| 5,443,246 A | 8/1995 | Peterson |
| 5,454,551 A | 10/1995 | Hobday |
| 5,476,252 A | 12/1995 | Yonezawa |
| 5,501,435 A | 3/1996 | Monteiro |
| 5,516,088 A | 5/1996 | Coffin, III |
| 5,529,297 A | 6/1996 | Sawdon |
| 5,580,035 A | 12/1996 | Ffield et al. |
| 5,582,379 A | 12/1996 | Keselman |
| 5,586,754 A | 12/1996 | Williams |
| 5,595,375 A | 1/1997 | Bennhausen |
| 5,615,968 A | 4/1997 | Verenski et al. |
| 5,657,972 A | 8/1997 | Blatt |
| 5,664,750 A * | 9/1997 | Cohen ................... 248/231.71 |
| 5,695,177 A | 12/1997 | Mascola |
| 5,704,577 A | 1/1998 | Gordon |
| 5,727,899 A | 3/1998 | Dobrovolny |
| 5,733,061 A | 3/1998 | Child |
| 5,746,422 A | 5/1998 | Harada et al. |
| 5,807,333 A | 9/1998 | Osborne et al. |
| 5,820,116 A | 10/1998 | Haese |
| 5,826,310 A | 10/1998 | Hobday |
| 5,827,026 A | 10/1998 | Patti |
| 5,836,573 A | 11/1998 | Hayashi et al. |
| 5,868,710 A | 2/1999 | Battiato et al. |
| 5,873,386 A | 2/1999 | Arosio |
| 5,892,344 A | 4/1999 | Cooley |
| 5,899,445 A | 5/1999 | Kimble |
| 5,913,509 A | 6/1999 | Price et al. |
| 6,024,350 A | 2/2000 | Price et al. |
| 6,039,313 A | 3/2000 | Baculy |
| 6,073,285 A | 6/2000 | Ambach et al. |
| 6,073,920 A | 6/2000 | Colley |
| 6,079,703 A | 6/2000 | Chavez, Jr. |
| 6,102,383 A | 8/2000 | Tünkers |
| 6,109,602 A | 8/2000 | Schron, Jr. et al. |
| 6,139,000 A | 10/2000 | Price et al. |
| 6,241,231 B1 | 6/2001 | Schron, Jr. et al. |
| 6,326,059 B1 | 12/2001 | Lewin et al. |
| 6,338,478 B2 | 1/2002 | Baculy |
| 6,340,154 B1 | 1/2002 | Young |
| 6,382,576 B1 | 5/2002 | Heimbrock |
| 6,394,437 B1 | 5/2002 | Yonezawa |
| 6,402,130 B1 | 6/2002 | Price et al. |
| 6,402,131 B1 | 6/2002 | Baculy |
| 6,481,204 B1 | 11/2002 | Yuschak et al. |
| 6,520,495 B1 | 2/2003 | La Mendola |
| 6,619,599 B2 | 9/2003 | Elliott et al. |
| 6,634,823 B2 | 10/2003 | Sciortino |
| 6,644,636 B1 | 11/2003 | Ryan |
| 6,690,280 B2 | 2/2004 | Citrenbaum |
| 6,758,467 B2 | 7/2004 | Kitaura |
| 6,942,637 B2 | 9/2005 | Cartledge et al. |
| 6,942,647 B2 | 9/2005 | Cartledge et al. |
| 7,395,563 B2 | 7/2008 | Whitmore, III et al. |
| 2003/0019038 A1 | 1/2003 | Welling et al. |
| 2005/0006542 A1 | 1/2005 | Henning et al. |
| 2005/0267449 A1 | 12/2005 | Edoga et al. |
| 2006/0278785 A1 | 12/2006 | Wiesner et al. |
| 2007/0129634 A1 | 6/2007 | Hickey et al. |
| 2007/0220671 A1 | 9/2007 | Vanderheiden et al. |

* cited by examiner

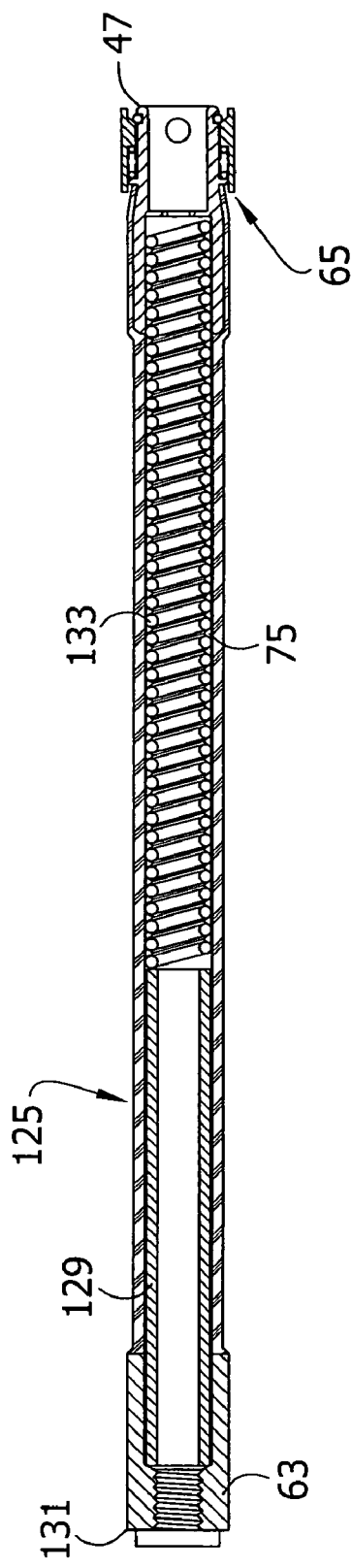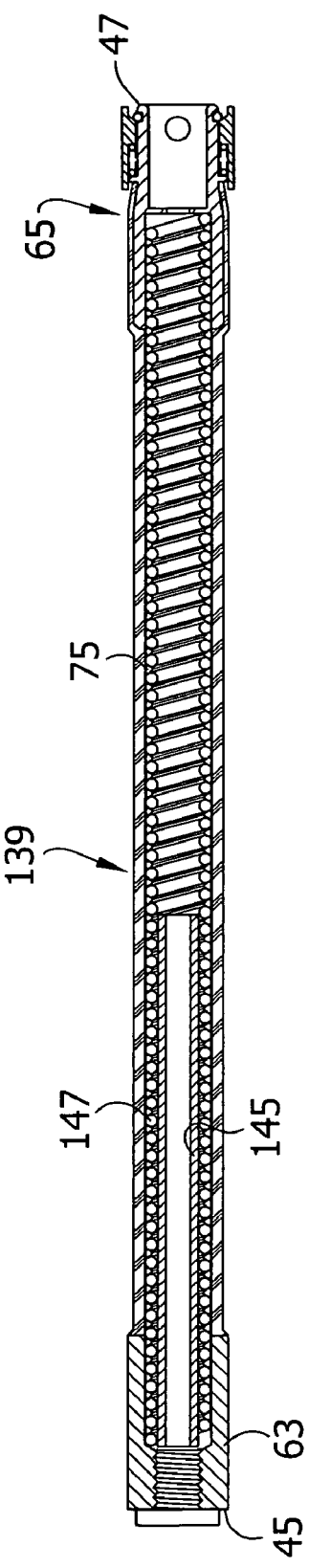

US 7,731,138 B2

FLEXIBLE CLAMPING APPARATUS FOR MEDICAL DEVICES

BACKGROUND OF THE INVENTION

This invention relates generally to the field of support apparatus for medical devices and more particularly to a medical device mounting apparatus having a flexible shaft.

Medical devices such as enteral feeding pumps are typically attached to an IV pole or other support member by a pole clamp or other attachment device that holds the pump in a fixed position relative to the support member. One existing pole clamp design allows one degree of freedom of motion of the pump relative to the pole by allowing the pump to be rotated or indexed between fixed orientations relative to the IV pole. However, existing pole clamp designs do not permit two or more degrees of freedom of motion of the pump such that the pump may be moved horizontally, vertically, or laterally relative to the IV pole for easier viewing and operation of the pump.

Such existing pole clamps are typically mounted directly on the housing of the pump so that the pump housing is in close proximity to the IV pole. As such, the pumps mounted by conventional pole clamps take up a large amount of vertical space on the IV pole that may be needed for other devices and/or medical fluid containers.

Furthermore, some existing pole clamp designs are limited in that they allow secure attachment of the feeding pump to a vertical cylindrical support structure such as an IV pole but cannot be readily mounted on other support structures such as a horizontal table top. Even if the clamp could be attached to some horizontal structure (e.g., a horizontally extending bed rail), the medical device would not be oriented properly for use. Such existing pole clamps do not allow an enteral feed pump or other medical device to be used outside of a hospital or medical care facility where vertical IV poles are unavailable and cumbersome for use.

SUMMARY OF THE INVENTION

In one aspect of the present invention, a clamping apparatus used in a medical environment to releasably secure a device to a support member generally comprises a flexible shaft having a first end for attachment to the support member and comprises a flexible shaft having a first end for attachment to the support member and a second end for attachment to the device. A clamp including a securing rod and a generally C-shaped clamping member at the first end selectively mounts the apparatus to the support member. The clamping member has an inner surface, an outer surface, and at least two apertures including a first aperture through which a securing rod passes and a second aperture for attachment of the flexible shaft.

In another aspect, a powered medical device assembly capable of selective mounting on a support generally comprises a powered medical device capable of use in at least one of diagnosing, monitoring and treating a patient. The medical device includes a housing and a display screen. A flexible shaft is adapted for connection to the medical device at a first end of the shaft and is adapted for connection to the support at a second end of the shaft. The flexible shaft is selectively configurable while connected to the medical device and to the support to permit the medical device to be moved from a first position in which the medical device is retained by the flexible shaft so that a point on the medical device is a first distance away from the support to a second position in which the medical device is retained by the flexible shaft so that the point on the medical device is a second distance different from the first distance from the support.

Other objects and features of the present invention will be in part apparent and in part pointed out hereinafter.

BRIEF DESCRIPTION OF THE DRAWINGS

FIG. 6B is a longitudinal section of a first modified flexible shaft;

FIG. 6C is a longitudinal section of a second modified flexible shaft;

Corresponding reference characters indicate corresponding parts throughout the several views of the drawings.

DETAILED DESCRIPTION OF THE PREFERRED EMBODIMENTS

Figure 1:
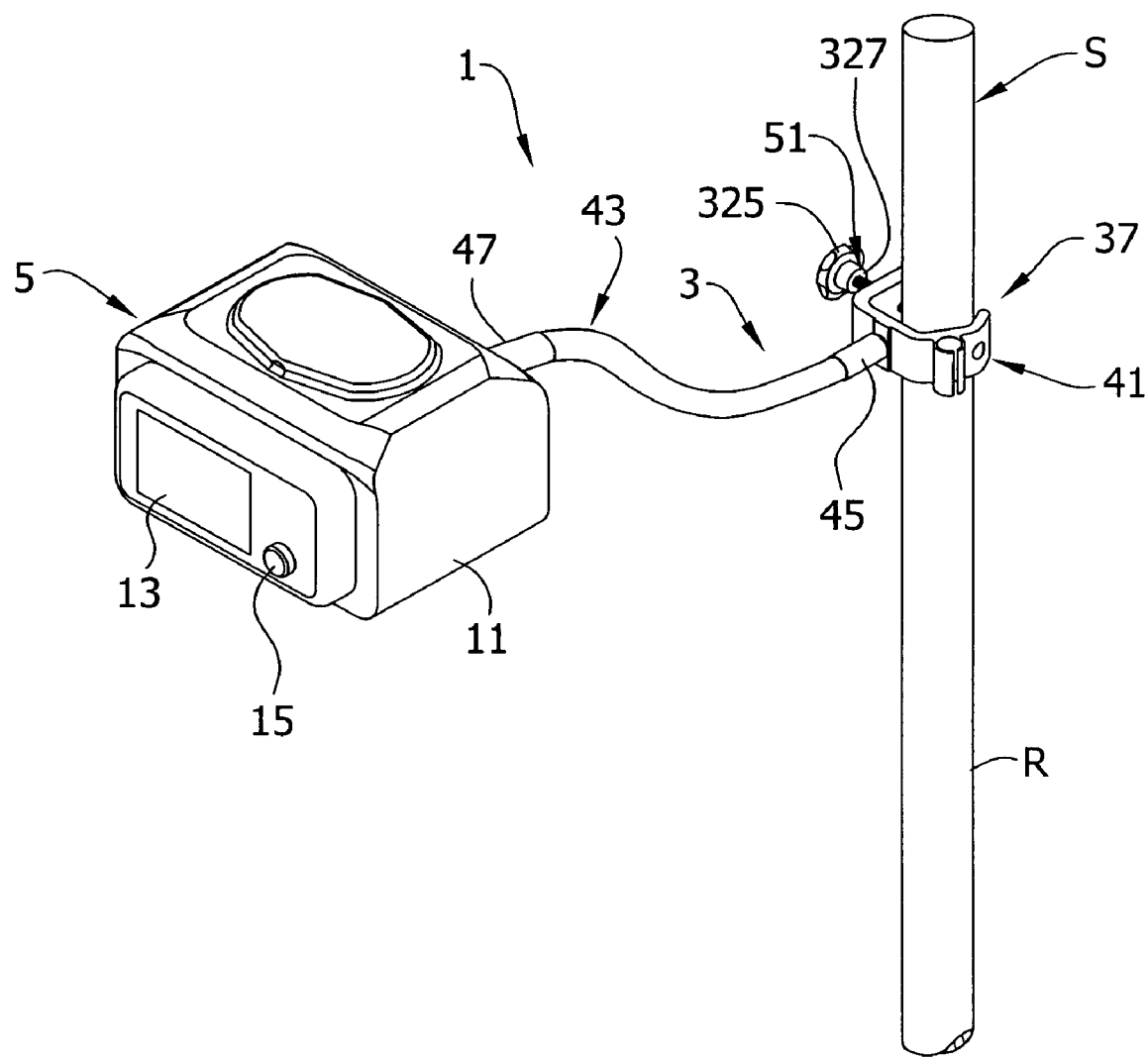
FIG. 1 is a perspective of a first embodiment of a clamping apparatus mounting an enteral feeding pump to an IV pole.
Figure 2:
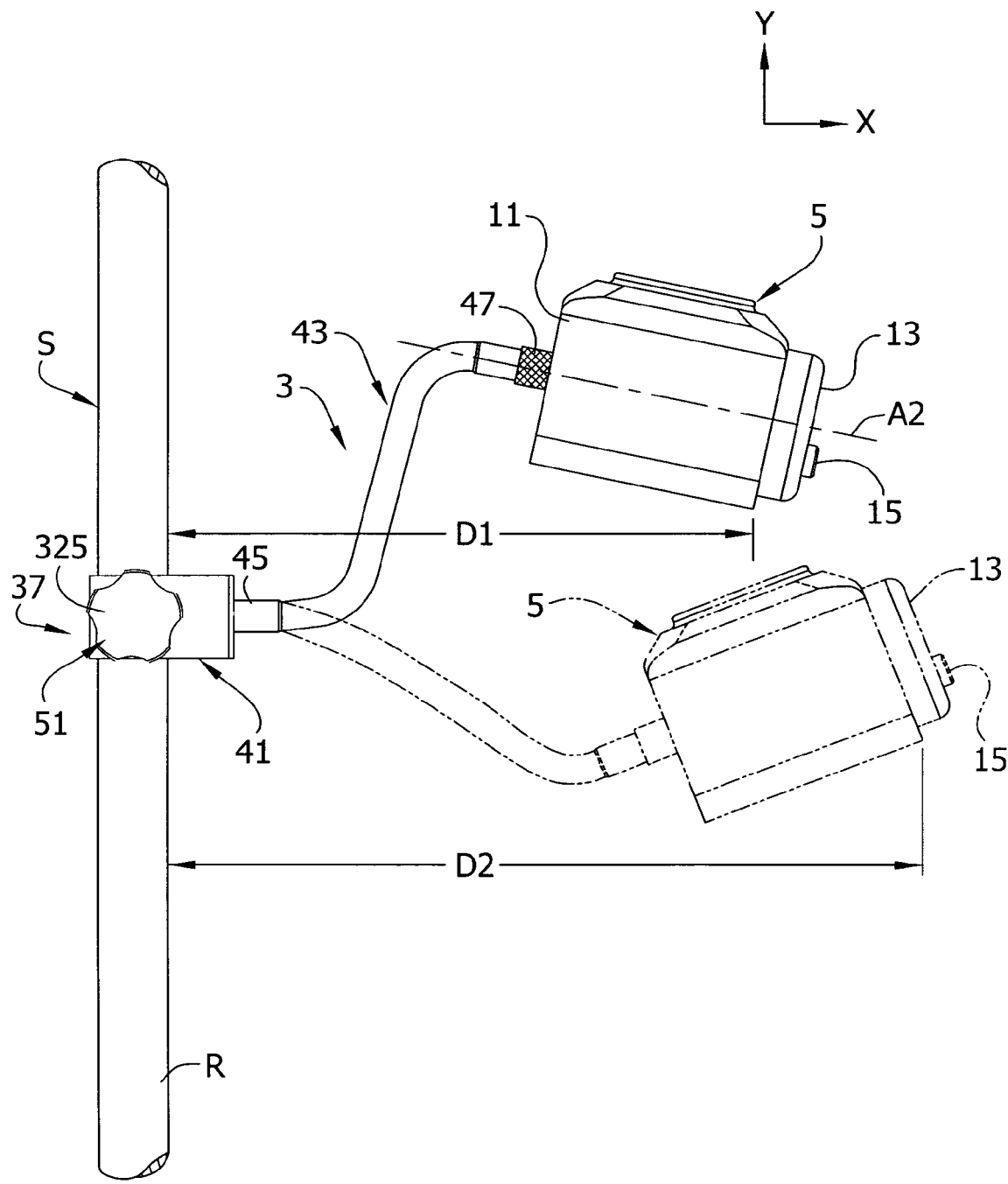
FIG. 2 is a left side elevation of FIG. 1.

Referring now to the drawings and in particular to FIGS. 1 and 2, a powered medical device assembly 1 includes a clamping apparatus 3 releasably attached to a support member S to support a medical device 5 on the support member (the reference numerals designating their subjects generally). In the embodiment of FIG. 1, the support member S is a vertical IV pole (broadly, "a support member) having a cylindrical rod R extending up from a stand (not shown) that is commonly used to support medical paraphernalia such as IV bags (not shown) in a hospital or other healthcare environment. As discussed further below, the clamping apparatus 3 is capable of mounting the medical device 5 on support members having other than cylindrical shapes. The clamping apparatus 3 is configured to allow full range of motion (i.e., six-degrees of freedom of motion) of the medical device 5 relative to the support member S so the medical device can be positioned for better viewing and adjustment. The clamping apparatus 3 may be more broadly described as "mounting apparatus", as it will be understood that apparatus that mounts a medical device without clamping (e.g., including even a permanent attachment) falls within a broader scope of the present invention.

Figure 3:
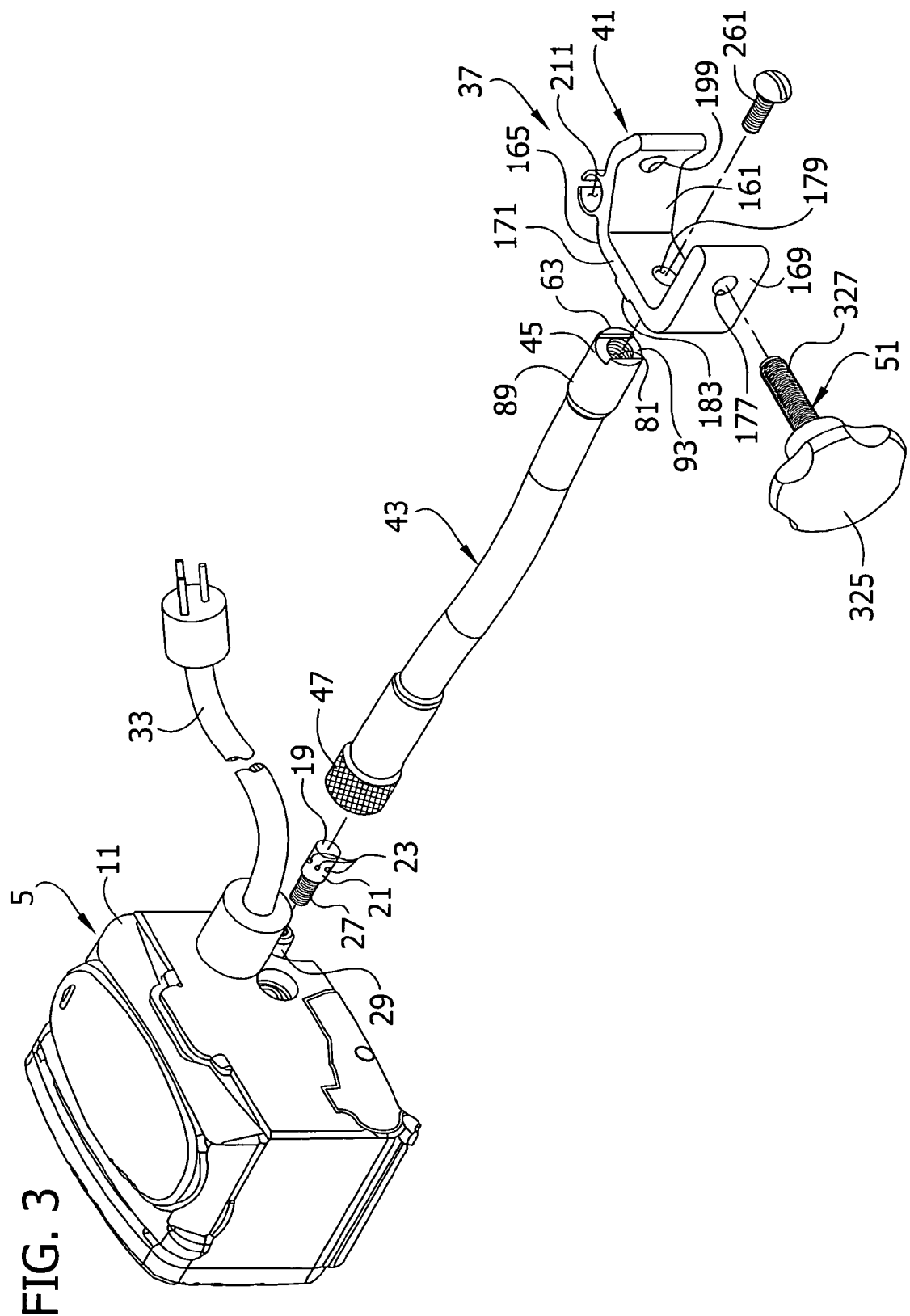
FIG. 3 is a rear perspective of the clamping apparatus and medical device with the clamping apparatus exploded.

The medical device 5 may be any medical device used in diagnosing, monitoring, or treating a patient. In the illustrated embodiment, the medical device 5 is an enteral feeding pump used to regulate the delivery of nutritional fluids to a patient from a container (not shown) but it is understood that the medical device could be any other type of device that is typically mounted on a support. The pump 5 has a housing 11 and a display screen 13 at the front of the housing for monitoring the operational status of the pump and a control knob 15 for making adjustments to the pump. As shown in FIG. 3, the pump 5 has a mounting stud 19 attached to the back of the housing 11 for releasable attachment to the clamping apparatus 3. The mounting stud 19 is cylindrical and has a radial external surface with recesses 23 and a threaded nipple 27 for mating with a threaded hole 29 on the housing 11. The pump 5 has an electrical cord 33 attached to the housing 11 for connection to an electrical outlet (not shown) to provide power to the pump. It is understood that the pump 5 may be battery operated so that the cord 33 may be omitted from the pump without departing from the scope of this invention. It is envisioned that the pump 5 may also be fluid (e.g., air) powered.

The clamping apparatus 3 includes a clamp, generally indicated 37, having a clamping member, generally indicated 41, for releasable attachment of the assembly 1 to the support member S and a securing rod 51 releasably attached to the clamping member for attaching the apparatus to the IV pole. The clamping apparatus 3 includes a flexible shaft, generally indicated 43, attached to the clamping member 41 at a first end 45 and releasably attached to the medical device 5 at a second end 47. The flexible shaft 43 is selectively configurable while connected to the pump 5 to allow the pump to have complete freedom of motion relative to the support member S. The complete freedom of motion of the pump 5 relative to the support member S includes translation of the pump in any of the three dimensions (e.g., x, y, and z-axis) relative to the support as well as rotation or the ability to change the angle of orientation of the pump relative to any of the three axes so that the pump has six degrees of freedom of motion relative to the support. Moreover, once moved the clamping apparatus 3 retains the medical device 5 in its new selected position.

Figure 4:
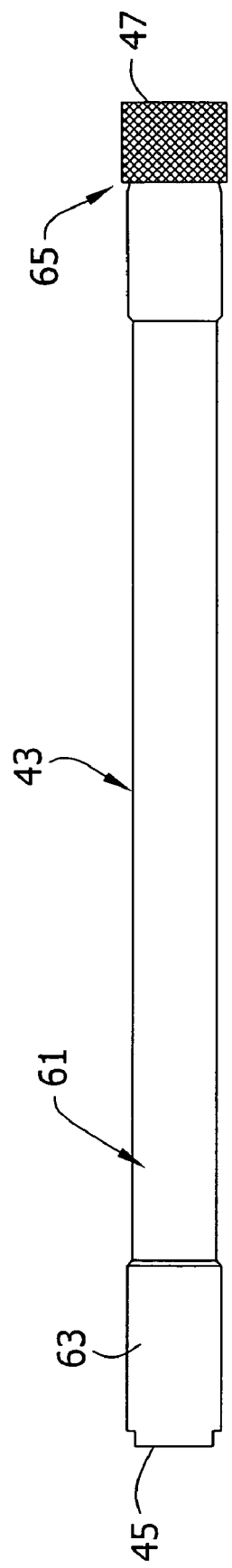
FIG. 4 is a side elevation of a flexible shaft of the clamping apparatus.
Figure 5:
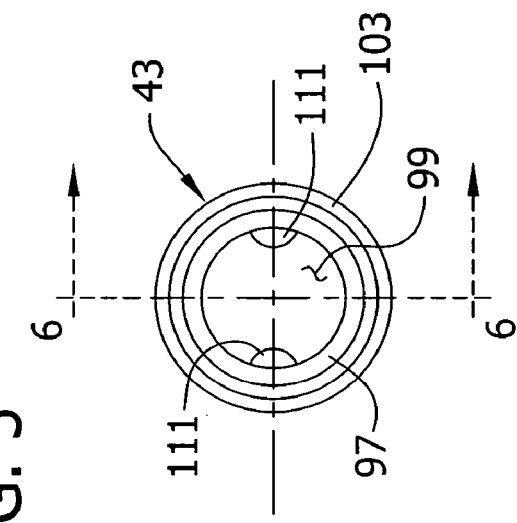
FIG. 5 is an end view of the flexible shaft.
Figure 6:
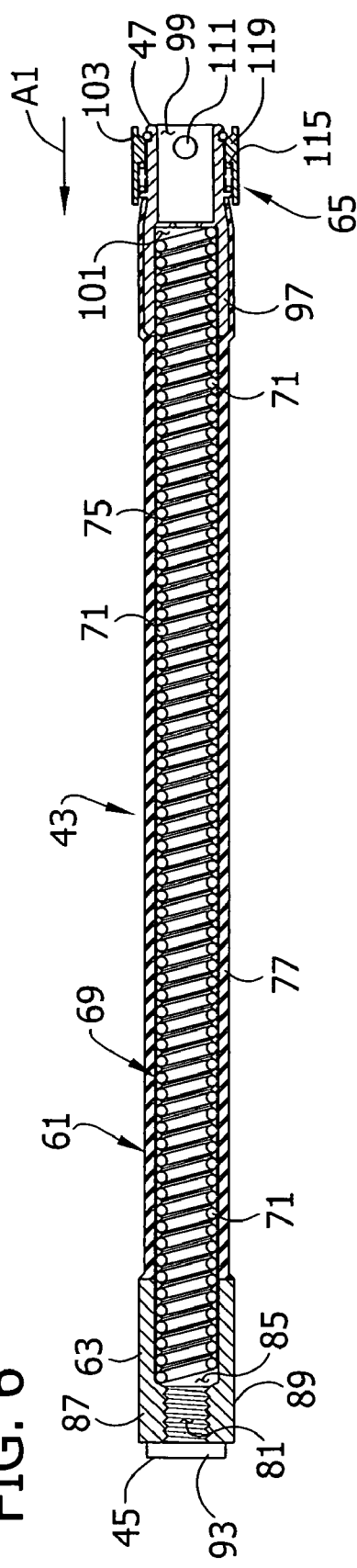
FIG. 6 is a section of the shaft taken in the plane including line 6-6 of FIG. 5.

As shown in FIGS. 4-6, the flexible shaft 43 has a generally tubular body, generally indicated 61, with an internally threaded bushing 63 mounted on the body at the first end 45 of the shaft and a quick-release connector (locking collar), generally indicated 65, mounted on the body at the second end 47 of the shaft. As shown in FIG. 6, the tubular body 61 includes a coil spring, generally indicated 69, having a plurality of coils 71 extending from the first end 45 to the second end 47 of the shaft 43. A stiffener 75 is disposed between the coils 71 to provide stiffness to the flexible shaft 43 and allow the shaft to be set in a stationary position when bent. In the illustrated embodiment, the stiffener 75 comprises a wire having a triangular cross-section but it is understood that the stiffener may have other shapes. The stiffener 75 is pliable to allow the spring 69 to bend and twist in any direction but provides sufficient resistance to prevent the spring from returning to its original position and shape. A sheath 77 covers the spring 69 and the stiffener 75 to provide a thin outer layer for the flexible shaft 43. The sheath 77 may be made from plastic, rubber, vinyl, or any other flexible material.

Referring now specifically to FIG. 6, the threaded bushing 63 mounted on the first end 45 of the flexible shaft 43 has a threaded axial bore 81 at its outer end that opens to an axial cavity 85 at its inner end that receives the spring 69 and the stiffener 75 of the flexible shaft 43. The threaded bushing 63 has a collar 87 surrounding the threaded bore 81 that forms an external surface 89 of the flexible shaft 43 that may be grasped for connecting the threaded bushing to the clamping member 41. As shown in FIG. 3, the outer axial surface of the bushing has a rectangular notch 93 slightly greater in width than the diameter of the threaded bore 81.

Figure 6A:
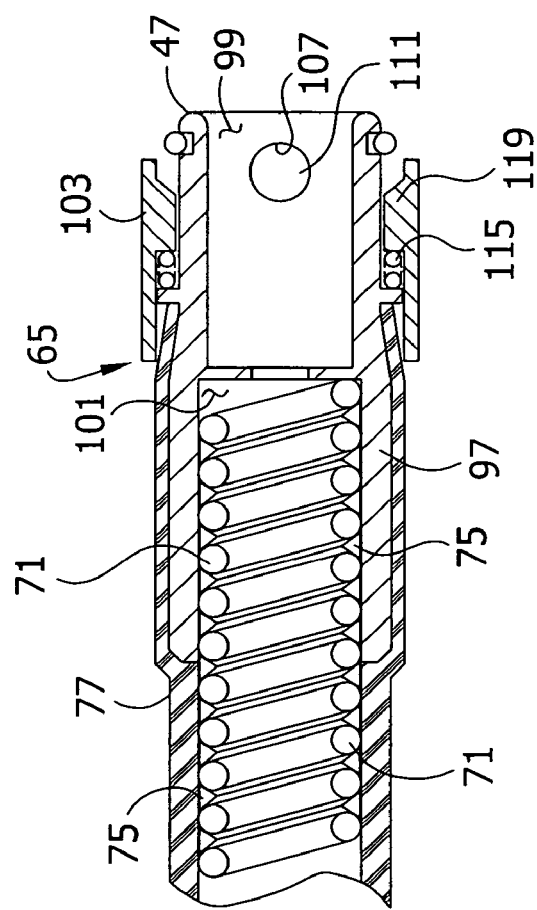
FIG. 6A is an enlarged detail of FIG. 6 showing a sleeve of the flexible shaft in a release position.

The quick release connector 65 is a "quick-disconnect" type connector for releasable connection between the flexible shaft 43 and the mounting stud 19 on the pump 5. As shown in FIGS. 6 and 6A, the quick release connector 65 includes a bushing 97 having an axially outer cavity 99 for receiving the mounting stud 19, an axially inner cavity 101 for receiving the spring 69 and stiffener 75, and a connector actuating structure (sleeve) 103 slidable on the bushing. The bushing 97 has radial openings 107 that open to the outer cavity 99 of the bushing. Detent elements 111 are housed in the openings 107 and protrude, at least in part, through the radial openings into the outer cavity 99. In the illustrated embodiment the connector 65 has two detent elements 111 in the form of metal balls spaced apart 180 degrees and received in respective radial openings 107 in the bushing. It is understood that the quick release connector 65 could have more or less than two detent elements 111, the detent elements may be other than spherical, and the detent elements may be radially spaced more or less than 180 degrees without departing from the scope of this invention.

The sleeve 103 is slidable on the bushing 97 between an attach position (FIG. 6) and a release position (FIG. 6A). A spring 115 mounted on the bushing 97 biases the sleeve 103 to the attach position. The sleeve 103 has a shoulder 119 that contacts the balls 111 at the attach position to urge the balls radially inward so that a portion of the balls protrudes into the outer cavity 99 and to lock the balls to prevent radial movement of the balls away from the central axis of the bushing 97. The sleeve 103 is positioned in the release position by sliding the sleeve on the bushing 97 in the direction indicated by arrow A1 (FIG. 6) toward the second end 47 of the flexible shaft 43 to compress the spring 115. In the release position of FIG. 6A, the shoulder 119 is free from engagement with the balls 111 so that the balls may move radially outward away from the outer cavity 99 of the bushing 97.

It is understood that the flexible shaft 43 is releasably attached to the pump by holding the sleeve 103 of the quick-release connector 65 in the release position and placing the bushing 97 over the mounting stud 19 on the housing so that the external surface 21 of the mounting stud is received into the outer cavity 99 of the bushing. The bushing 97 and flexible shaft 43 may be rotated as needed so that the balls 111 align with the locking recesses 23 on the outer surface 21 of the mounting stud 19. When the balls 111 are received in the recesses 23, the sleeve 103 is released so that the spring 115 urges the sleeve to the attach position and the shoulder 119 engages the balls to bias the balls radially inward to form a secure locking connection between the flexible shaft 43 and the pump 5. The engagement of the balls 111 with the locking recesses 23 on the mounting stud 19 provides an audible signal in the form of a "clicking" sound that provides confirmation that the pump 5 is locked on the flexible shaft 43. To release the pump 5 from the connector 65, the sleeve 103 is slid to the release position and the mounting stud 19 may be disengaged from the bushing 97 as the balls 111 are free to move radially outward from the outer cavity 99 so that the balls can move out of the recesses 23 to remove the stud from the outer cavity. Thus, the sleeve 103 may be moved linearly and without rotation between the attach position and the release position of the quick-release connector 65 to allow rapid disengagement of the pump 5 from the flexible shaft 43. It will be understood that other types of connections for the pump 5 and flexible shaft 43 may be used without departing from the scope of the present invention.

As shown in FIG. 6B in a modified version of the flexible shaft, generally indicated 125, the shaft may include a tube stiffener 129 made out of rigid material (e.g., copper, plastic, etc.) adjacent the second end 131 of the flexible shaft. The tube stiffener 129 replaces a portion of the spring 133 at the second end 131 of the flexible shaft so that the flexible shaft is substantially rigid along the axial length of the tube stiffener and the portion and is flexible along the axial length of the spring 133.

FIG. 6C shows another modified version of the flexible shaft, generally indicated 139, including an internal stiffener 145 received through the middle of the coil spring 147. The internal stiffener 145 increases the stiffness of the flexible shaft 139 but still allows the entire length of the flexible shaft to flex. The internal stiffener 145 increases the amount of weight that can be supported in a stationary position at either end of the flexible shaft 139. It is understood that the tube stiffener 129 (FIG. 6B) and the internal stiffener 145 may range in axial length depending on the specific amount of rigidity or stiffness required in the flexible shaft 125, 139.

Figure 7:
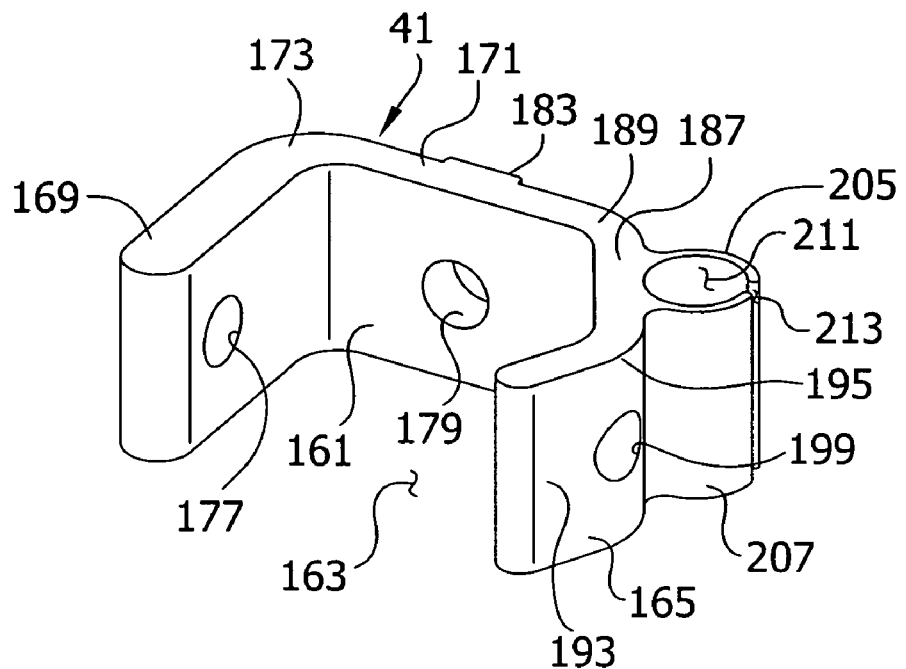
FIG. 7 is an enlarged perspective of a first version of a clamping member of the clamping apparatus.
Figure 8:
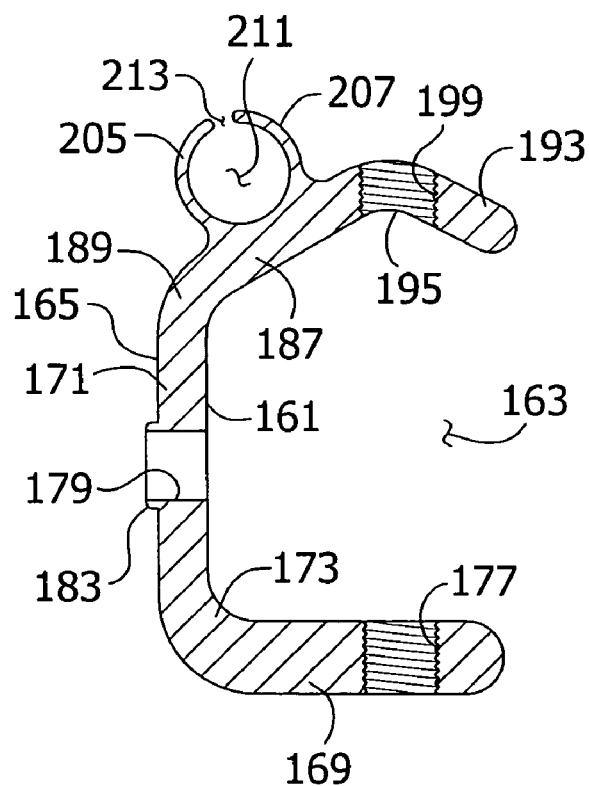
FIG. 8 is a horizontal section of the clamping member of FIG. 7.

As shown in FIGS. 7 and 8, the clamping member 41 is generally C-shaped and has an inner surface, generally indicated 161, for contact with the IV pole or other support member S, an opening 163 for receiving the support member, and an outer surface generally indicated 165. As shown in the orientation of FIG. 8, the clamping member 41 has a lower portion 169 at the bottom of the clamping member generally perpendicular to a middle portion 171 so that the lower portion and middle portion meet at a bend 173 having an angle of approximately 90 degrees. A lower threaded hole 177 of the clamping member 41 passes through the lower portion 169 and a cylindrical, non-threaded opening 179 passes through the middle portion 171. The middle portion 171 has a rectangular shoulder 183 protruding from the outer surface 165 of the clamping member 41. The shoulder 183 is sized to be received in the rectangular notch 93 (FIG. 3) on the threaded bushing 63 at the first end 45 of the flexible shaft 43 when the flexible shaft is connected to the clamping member 41.

A first upper portion 187 of the clamping member 41 is upwardly bent relative to the middle portion 171 so that the middle portion and the first upper portion meet at a bend 189 having an angle greater than 90 degrees. A second upper portion 193 is downwardly bent relative to the first upper portion 187 so that the first and second upper portions meet at an upper bend 195 in the clamping member 41. An upper threaded hole 199 is located on the upper bend 195 between the first and second upper portions 187, 193 so that the upper hole is axially aligned with the lower hole 177 in the lower portion 169 of the clamping member 41.

As shown in FIGS. 7 and 8, the first upper portion 187 has two roughly semi-cylindrical protrusions 205, 207 on its outer surface that form a cylindrical recess 211 in the first upper portion. The cylindrical recess 211 provides a storage area for an AC power adapter cord (not shown) when the cord is not in use. The two protrusions 205, 207 are separated by an axial slot 213 that allows the power adapter cord or other cord of the pump 5 to be received in the recess 211.

Figure 9:
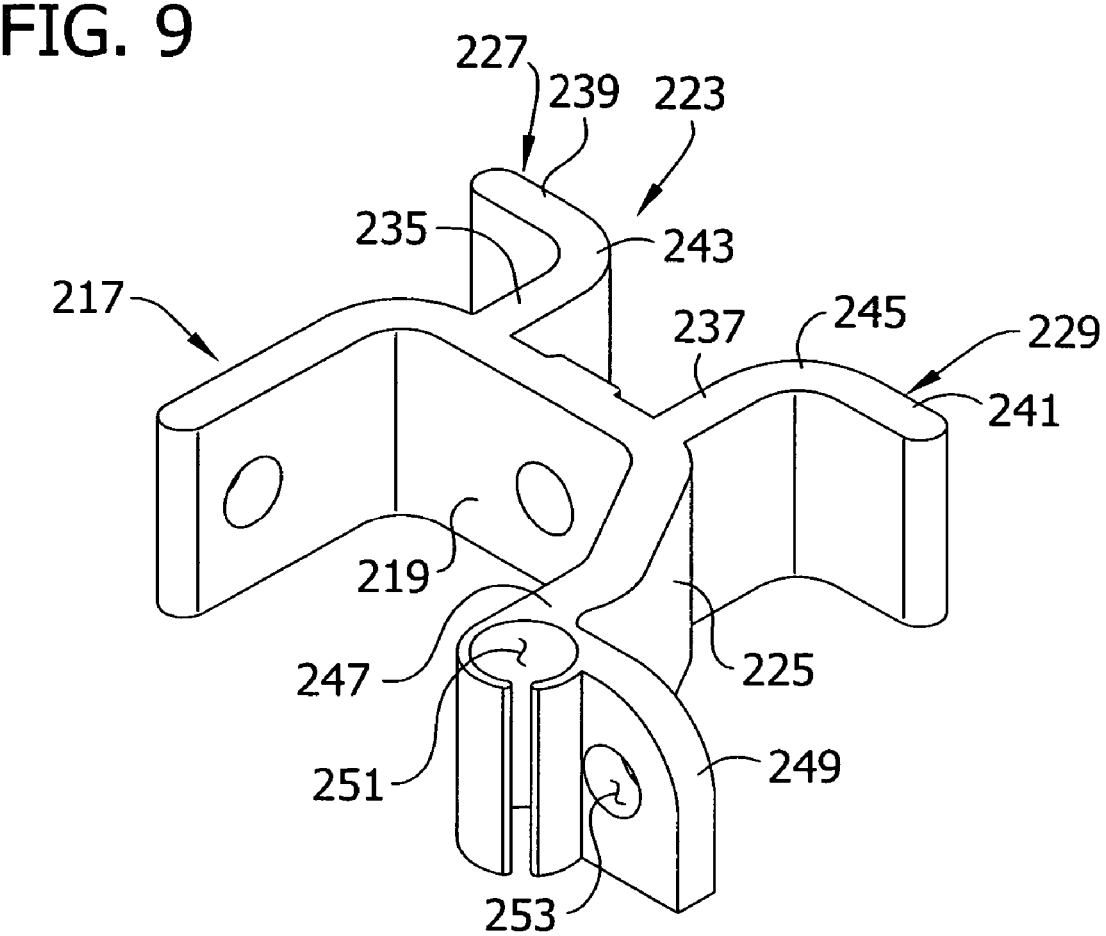
FIG. 9 is an enlarged perspective of a second version of the clamping member.

FIG. 9 shows another version of the clamping member 217 that is substantially similar to the embodiment of FIG. 7 but the middle portion 219 of the clamping member has a bracket, generally indicated 223, on its outer surface 225 for storing an electrical cord 33 (FIG. 3) or other cable of the pump 5. In the embodiment of FIG. 9, the bracket 223 includes two L-shaped fingers generally indicated 227, 229 protruding from the outer surface 225 of the middle portion 219 of the clamping member 217 that are spaced apart in an opposed (back-to-back) orientation. Each finger 227, 229 has a respective first portion 235, 237 and respective second portion 239, 241 joined by a 90 degree bend 243, 245. The second portion 239, 241 of a respective finger 227, 229 retains the electrical cord 33 (FIG. 3) on the first portion 235 when the cord is wrapped around the bracket 223.

The second upper portion 247 of the clamping member 217 of FIG. 9 has a tab 249 adjacent the cylindrical recess 251 and protruding from the outer surface 225 of the clamping member. The tab 249 provides for direct attachment of the clamping member 217 to the housing 11 of the pump 5 (i.e., omitting flexible shaft 43, 125, 139). The tab 249 has a cylindrical hole 253 for receiving a threaded fastener (not shown) that attaches the clamping member 217 directly to the pump housing 11. In the illustrated embodiment the cord bracket 223 and tab 249 are integrally formed with the C-shaped clamping member 217 but it is understood that the bracket and/or tab could be separate parts that may be attached to the clamping member by welding or other attachment methods.

As shown in FIG. 3, the flexible shaft 43 is attached to the clamping member 41 by a threaded bolt 261 or other fastener that is received through the opening 179 in the middle portion 171 of the clamping member and is in threaded engagement with the threaded bushing 63 on the first end 45 of the flexible shaft. When the axially outer surface of the threaded bushing 63 on the flexible shaft 43 abuts the outer surface 165 of the middle portion 171 of the clamping member 41, the shoulder 183 on the middle portion of the clamping member is received in the notch 93 on the threaded bushing to align the shaft with the clamping member. Also, the engagement of the notch 93 on the threaded bushing 63 and the shoulder 183 on the clamping member 41 prevents the bushing from rotating when the threaded fastener 261 is threadably advanced into the bushing. The threaded connection between the flexible shaft 43 and the clamping member 41 allows the flexible shaft and the clamping member to be disassembled and interchanged with other parts (e.g., a flexible shaft having a longer or shorter length, a flexible shaft having an increased or decreased stiffness, or a clamping member having a different shape) by removing the threaded fastener 261. It is understood that the flexible shaft 43 may be connected to the clamping member 41 with other attachment mechanisms (e.g., quick-disconnect connector, rivet, etc.) without departing from the scope of this invention.

Figure 10:
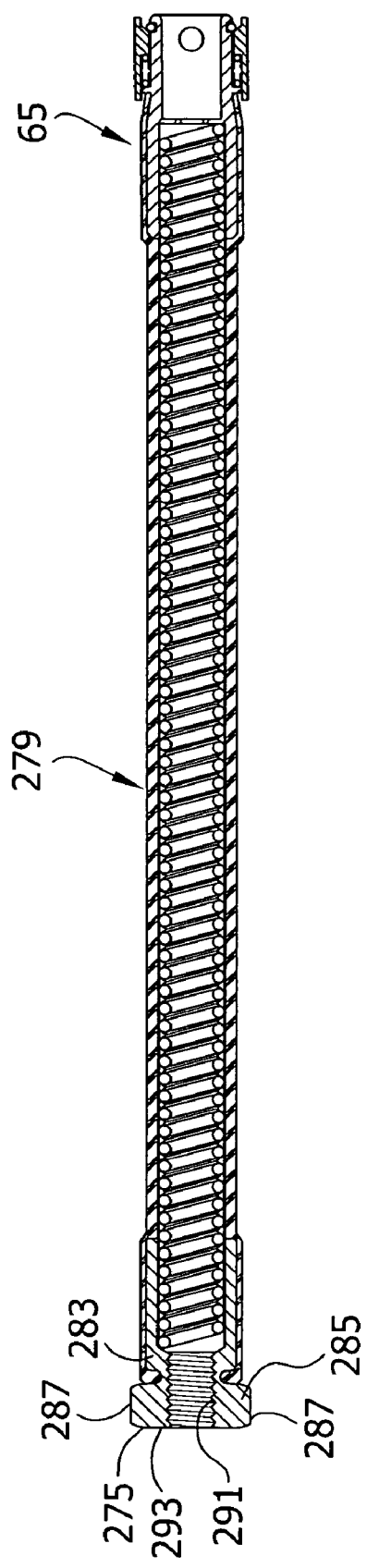
FIG. 10 is a longitudinal section of a flexible shaft of a clamping apparatus of a second embodiment.
Figure 11:
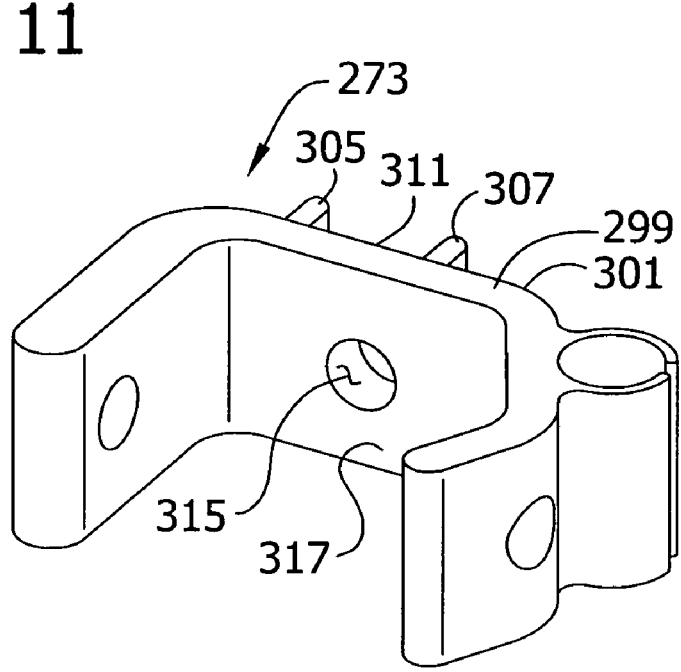
FIG. 11 is a perspective of a clamping member of the clamping apparatus of the second embodiment.
Figure 12:
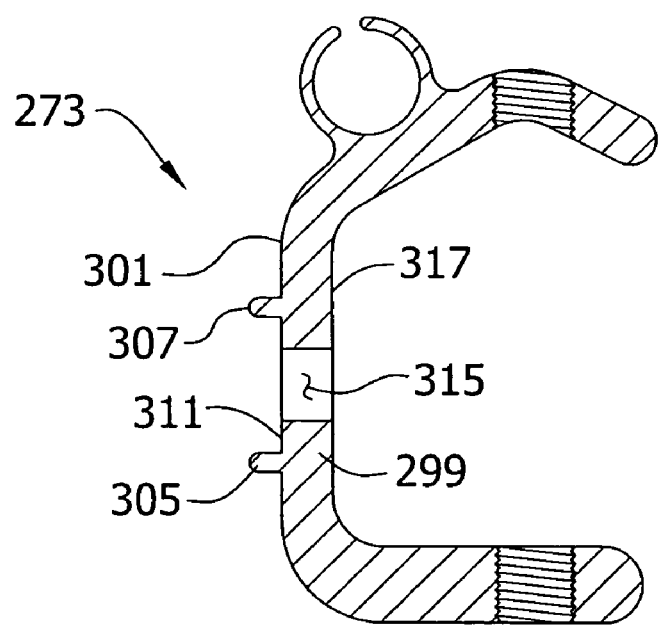
FIG. 12 is a horizontal section of the clamping member of FIG. 11.

FIGS. 10-12 show components of a clamping apparatus of a second embodiment having an alternative connection between the clamping member 273 and the first end 275 of the flexible shaft 279. As shown in FIG. 10, the flexible shaft 279 of this embodiment has a threaded bushing 283 at its first end 275 with a hex head fitting 285 having six radial flats 287 (only two of which are shown in FIG. 10) at the radially outer surface of the threaded bushing. The bushing 283 has a threaded bore 291 for receiving the threaded fastener (not shown, but the same as the fastener shown in FIG. 3) and a flat outer axial surface 293 at the first end 275 of the flexible shaft 279.

FIGS. 11-12 show the clamping member 273 having a middle portion 299 for mating with the flat outer axial surface 293 of the threaded bushing 283 of FIG. 10. The outer surface 301 of the middle portion 299 of the clamping member 273 has two spaced apart shoulders 305, 307 and a substantially flat contact surface 311 between the shoulders. The cylindrical opening 315 in the middle portion 299 of the clamping member 273 is centrally located opening from the inner surface 317 of the clamping member to the flat contact surface 311 on the outer surface 301 of the clamping member.

In this embodiment, the flexible shaft 279 is connected to the clamping member 273 by axially aligning the threaded bore 291 of the bushing 283 with the cylindrical opening 315 in the middle portion 299 of the clamping member. The flat outer axial surface 293 of the threaded bushing 283 abuts against the flat contact surface 311 of the clamping member 273 so that the threaded fastener 261 (FIG. 3) passes through the cylindrical opening 315 and connects the flexible shaft 279 and the clamping member. The distance between the shoulders 305, 307 on the outer surface 301 of the middle portion 299 is such that opposed radial flats 287 of the hex head fitting of the threaded bushing 283 fit between the shoulders so that the bushing is prevented from rotating when the threaded fastener 261 is advanced into the threaded bore 291. The engagement of the shoulders 305, 307 with a respective radial flat 287 of the hex head fitting 285 of the threaded bushing 283 allow the threaded fastener 261 to be advanced in the threaded bore 291 of the bushing without the use of a wrench or other tool to hold the threaded bushing in a stationary position during connection of the flexible shaft 279 to the clamping member 273.

Figure 13:
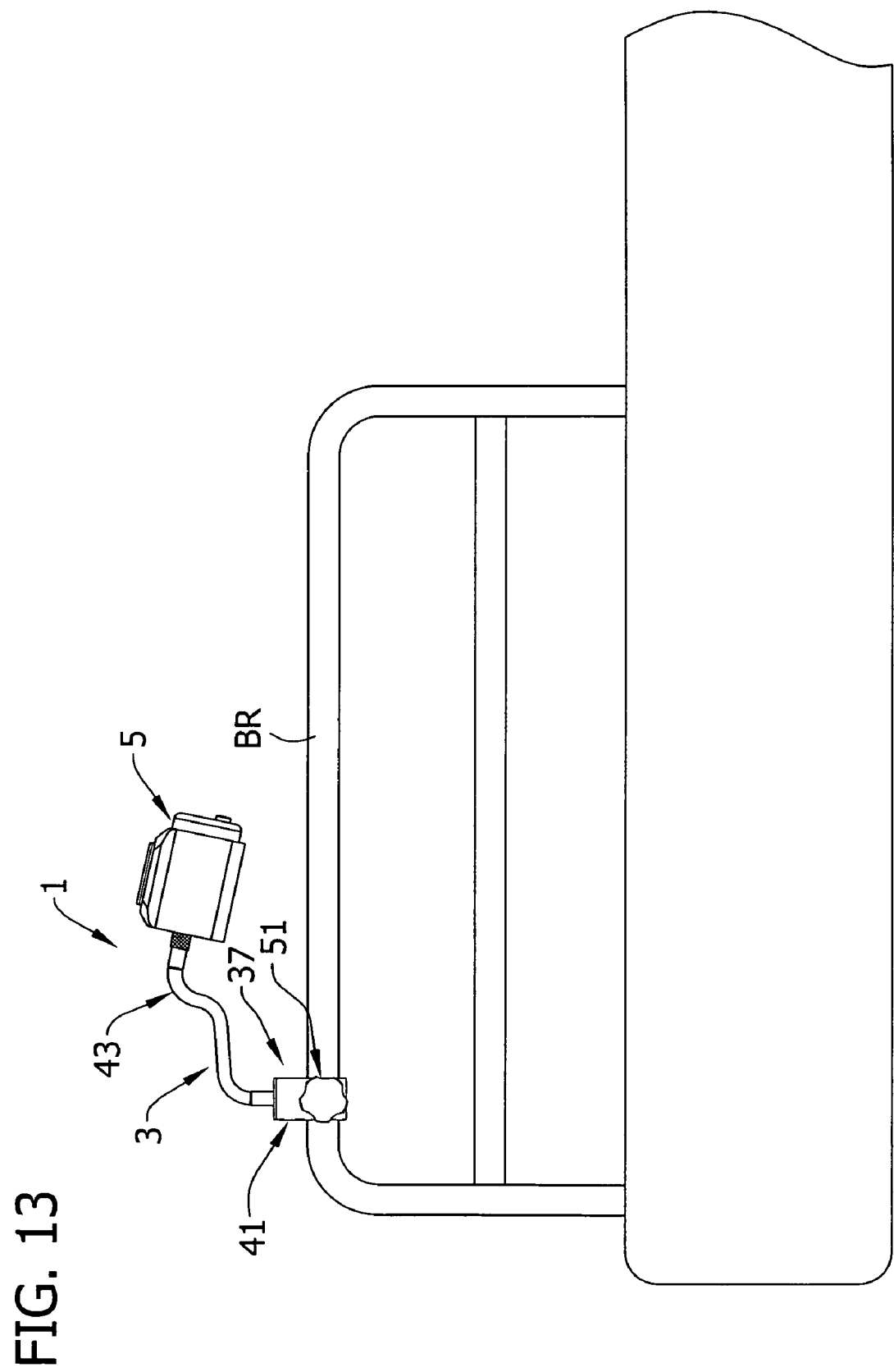
FIG. 13 is a fragmentary side elevation of a bed including a side rail having the first embodiment of the clamping apparatus attached thereto.
Figure 14:
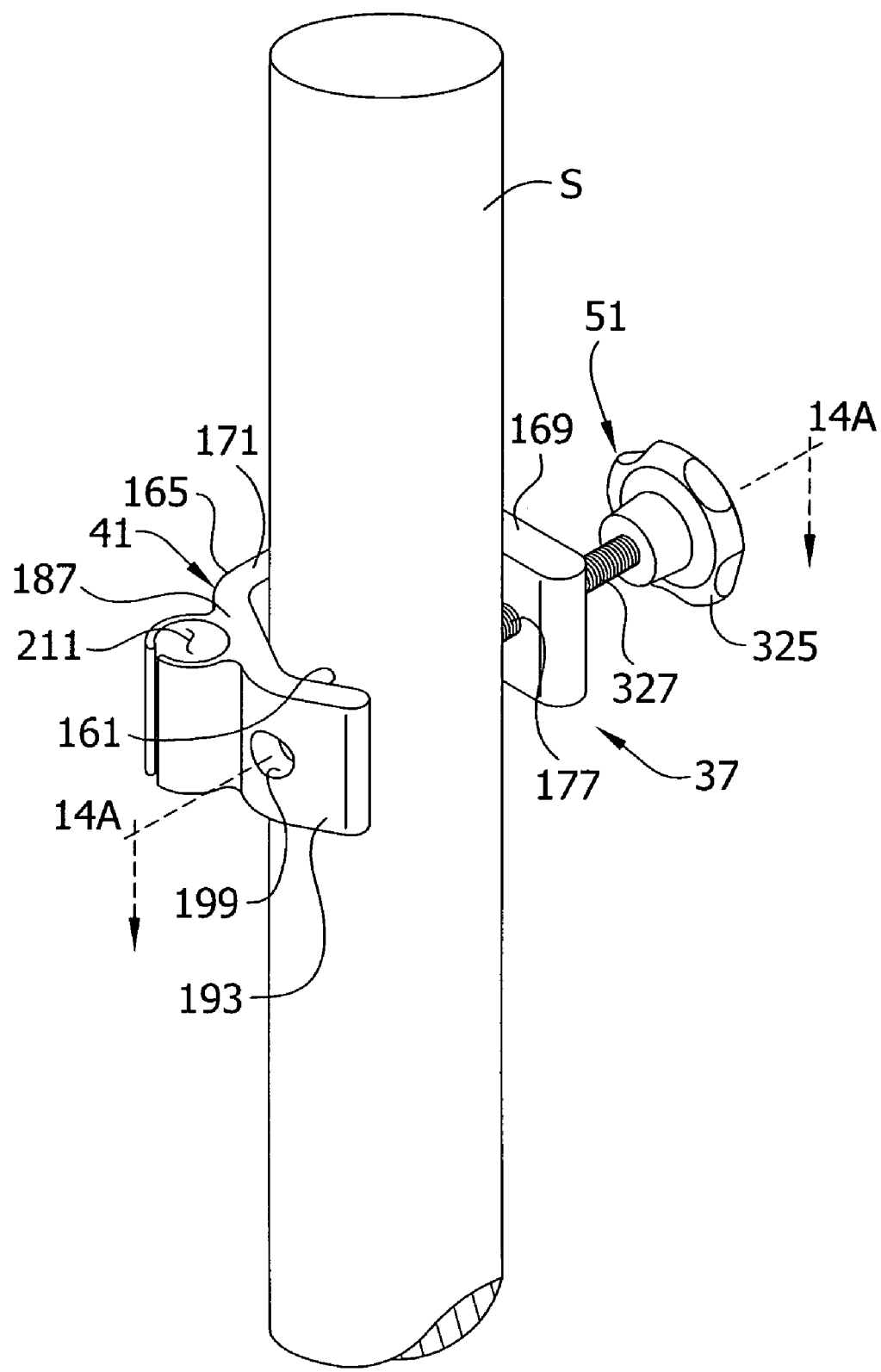
FIG. 14 is a perspective of the clamping apparatus of the first embodiment with the flexible shaft removed and a fragmentary portion of a cylindrical pole received in the clamping member.
Figure 14A:
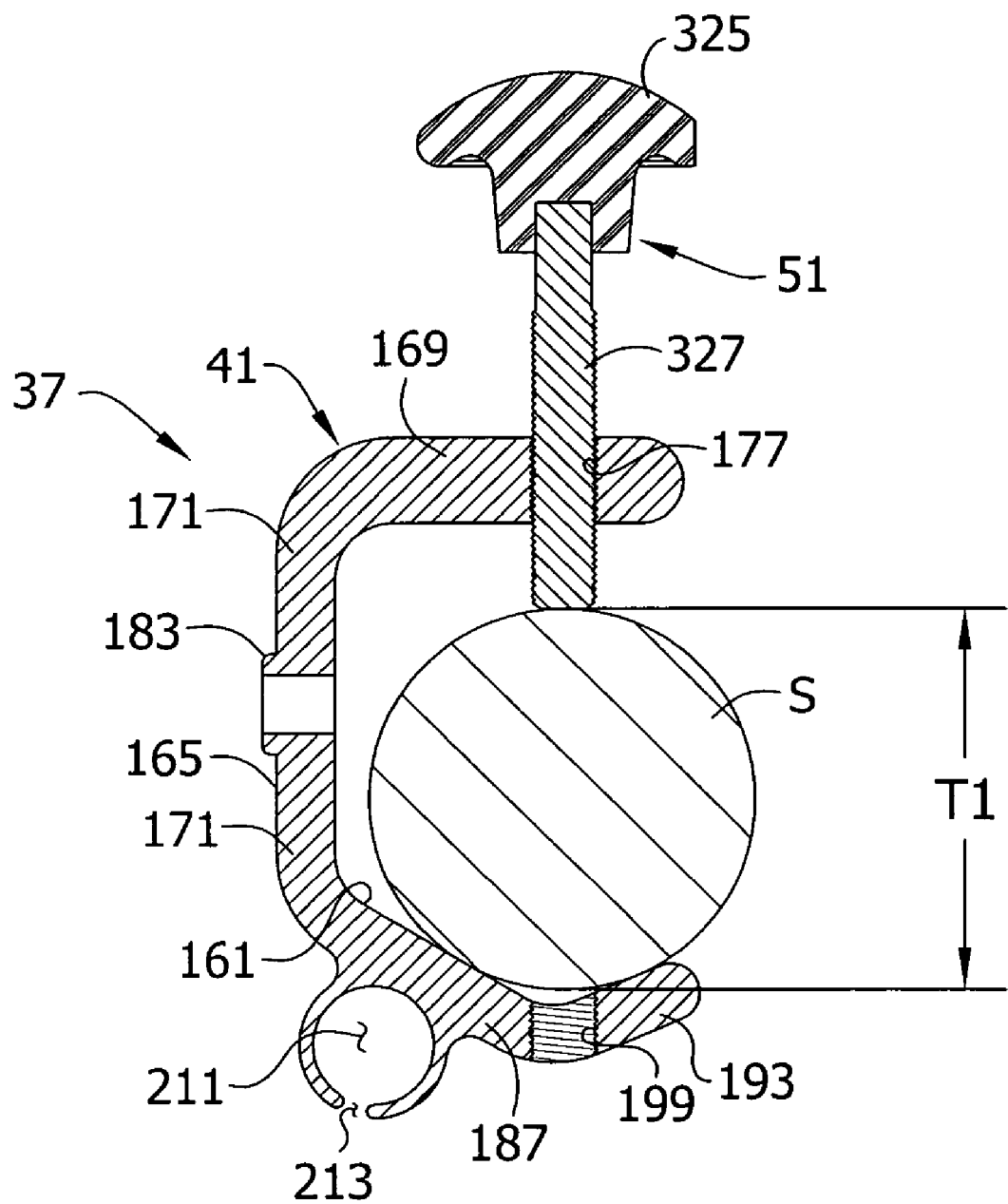
FIG. 14A is a cross-section taken along the plane including 14A-14A of FIG. 14.

The clamping member 41 attaches to the support member S by positioning the clamping member such that the support member is received through the opening 163 and contacts the inner surface 161 of the clamping member. The securing rod 51 has a knob 325 and a threaded stem 327 that threadably engages one of the upper and lower threaded holes 199, 177 of the clamping member 41 and contacts the support member S to secure the clamping member to the support member. The clamping member 41 of the present invention is shaped to receive support members S of various shapes so that the pump 5 may be mounted in a variety of locations. For example, the clamping apparatus 3 may be mounted on a pole such as a vertical IV stand S (FIGS. 1 and 2) or a horizontal bed rail pole BR (FIG. 13). As shown in detail in FIGS. 14 and 14A, the securing rod 51 is threadably inserted through the lower threaded hole 177 in the clamping member 41 so that the end of the securing rod contacts the outer surface of the pole S. The surface of the pole S opposite the securing rod 51 is positioned in contact with the first and second upper portions 187, 193 of the clamping member 41. The clamping apparatus 3 and the medical device assembly 1 are secured to the support member S by tightening the securing rod 51 so that the pole is in secure engagement with the clamping member 41.

Figure 15:
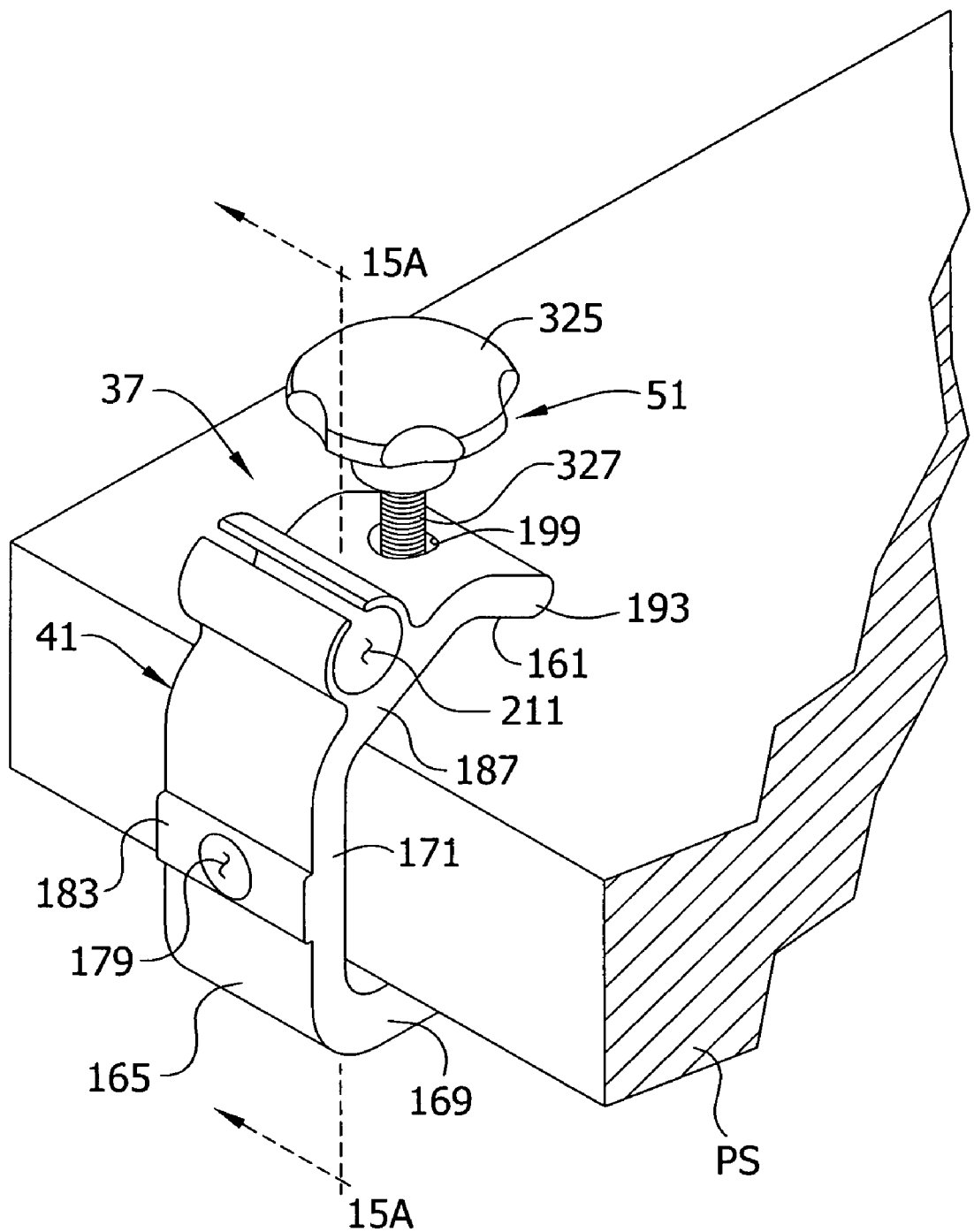
FIG. 15 is a perspective similar to FIG. 14 but with a fragmentary portion of a planar table top received in the clamping member.
Figure 15A:
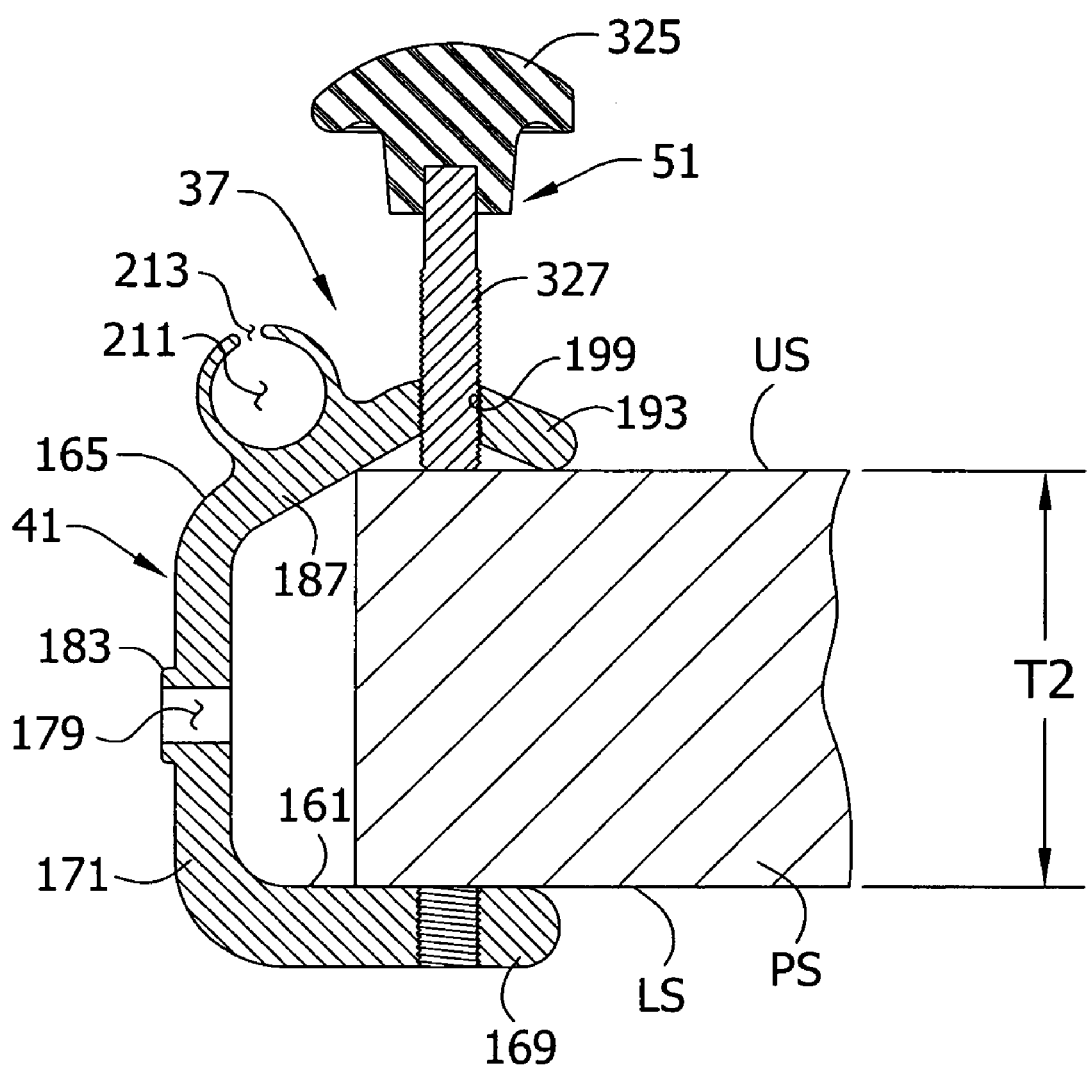
FIG. 15A is a cross-section taken along the plane including 15A-15A of FIG. 15.

As shown in FIGS. 15 and 15A, the clamping apparatus 3 may be configured for clamping the medical device 5 to a table top or other planar support member PS. In this arrangement, the securing rod 51 is threadably received through the upper threaded hole 199 of the clamping member 41 to contact the upper surface US of the table top PS. The lower surface LS of the table top PS contacts the inner surface 161 of the lower portion 169 of the clamping member 41 so that the table PS is held in clamped engagement between the securing rod 51 and the clamping member. The clamping apparatus 3 is secured to the table PS by turning the knob 325 on the securing rod 51 so that the rod engages the upper surface US of the table and urges the lower surface LS of the table into secure contact with the inner surface 161 of the clamping member 41.

It is understood that the clamping member 41 of the present invention allows the pump 5 to be mounted on either a cylindrical surface S (FIG. 14) or a planar surface PS (FIG. 15). Thus the pump 5 may be conveniently mounted in a health-care environment on an IV pole, horizontal or vertical bed rail, wheelchair tubing, or other support typical of a hospital or other medical facility. In addition, the pump 5 may be mounted on a table top PS or other structure for use in a home or other setting outside of a medical facility. Other suitable support structures for mounting the pump 5 include, but are not limited to, powered medical scooters or mobility chairs, multi-parameter carts, doors, tables, cabinets, bed stands, countertops, chairs, medical trays, television trays, and desks. Further, the clamping member 41 may receive a pole S having a first thickness T1 (FIG. 14A) or a table top PS having a generally planar surface with a thickness T2 (FIG. 15B) that may be greater than or less than the thickness of the pole.

The flexible shaft 43 of the present invention allows six degrees of freedom of motion of the pump 5 relative to the support member S. The pump 5 may be mounted in a first position (FIGS. 1 and 2) in which the pump is retained by the flexible shaft 43 in a stationary position so that a point on the housing 11 (e.g., the front of the housing) is a first distance D1 away from the support. By applying a force to the housing 11 of the pump 5, the flexible shaft 43 may be manipulated so that the pump is moved to a second position (shown in phantom in FIG. 2) in which the pump is retained by the flexible shaft in a stationary position so that the point on the housing is a second distance D2 greater than the first distance D1 from the support member S. It is understood that the pump 5 may be positioned closer to the pole S at the second position such that the distance D2 is less than the first distance D1. Also, the pump 5 may be tilted up or down about a horizontal axis (e.g., x-axis FIGS. 1 and 2) perpendicular to the support S and passing through the pump to allow better viewing of the display screen 13 on the pump. Further, the pump 5 may be tilted left or right about a vertical axis (e.g., y-axis FIGS. 1 and 2) to allow the display screen 13 to be viewed or the controls 15 to be accessed. The pump 5 may be twisted (i.e., rotated) about the horizontal axis A2 that may intersect the support S and the pump so that the screen 13 may be orientated for better viewing. It is understood that the pump 5 may be positioned such that the horizontal axis A2 does not intersect the support S without departing from the scope of this invention. The flexible shaft 43 also allows the pump 5 to be moved anywhere along a line intersecting the support S and the pump so that the only factor limiting the position of the pump relative to the support is the length of the flexible arm.

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the invention are achieved and other advantageous results attained.

As various changes could be made in the above constructions without departing from the scope of the invention, it is intended that all matter contained in the above description or shown in the accompanying drawings shall be interpreted as illustrative and not in a limiting sense. Further, all dimensional information set forth herein is exemplary only and is not intended to limit the scope of the invention. It is understood that any of the particular embodiments of the present invention may include one or more of the aspects or features of the invention as described herein and illustrated in the drawings.

What is claimed is:

1. A clamping apparatus for use in a medical environment to releasably secure a device to a support member, said clamping apparatus comprising:
   a flexible shaft having a first end for attachment to the support member and a second end for attachment to the device; and
   a clamp including a securing rod and a generally C-shaped clamping member at said first end for selectively mounting the apparatus to said support member, said clamping member having a lower portion, a middle portion extending generally upwardly from the lower portion, a first upper portion extending from the middle portion and upwardly bent relative to the middle portion, a second upper portion extending from the first upper portion and downwardly bent relative to the first upper portion forming a bend between the first and second upper portions, a first threaded aperture in the lower portion, a second threaded aperture in the bend and a third aperture in the clamp, the flexible shaft being attachable to the middle portion of the clamping member;
   the first and second threaded apertures each being configured for receiving the securing rod to mount the apparatus to said support member, the first aperture opening toward the first and second upper portions and the second aperture opening toward the lower portion.

2. A clamping apparatus as set forth in claim 1 wherein the clamping member comprises an inner surface having an opening sized to receive said support member, the clamp having a modular configuration such that the inner surface is adapted to receive a support member in the form of a pole and a support in the form of a planar support such that the inner surface contacts the support member at least two points of contact, the two points of contact being on the first end second upper portions, respectively.

3. A clamping apparatus as set forth in claim 1 further comprising a threaded fastener, and wherein the third aperture is a bore and the flexible shaft has a threaded bushing mounted on said first end, said clamping member being secured to the flexible shaft by the threaded fastener passing through the bore and mating with the threaded bushing.

4. A clamping apparatus as set forth in claim 3 wherein the clamping member has an outer surface and a shoulder extending from the outer surface, and the threaded bushing comprises a notch, the shoulder being sized to be received in the notch when the flexible shaft is connected to the clamping member to prevent rotation between the clamp and flexible shaft.

5. A clamping apparatus as set forth in claim 3 wherein said flexible shaft comprises a locking collar mounted for sliding, linear movement at said second end for quick release connection to the device, said locking collar having at least one detent element for releasable engagement with the device.

6. A clamping apparatus as set forth in claim 1 wherein the flexible shaft comprises a spring forming a part of the shaft and a rigid tube forming another part of the shaft.

7. A clamping apparatus for use in a medical environment to releasably secure a device to a support member, said clamping apparatus comprising:
   a flexible shaft having a first end for attachment to the support member and a second end for attachment to the device; and
   a clamp including a securing rod and a generally C-shaped clamping member at said first end for selectively mounting the apparatus to said support member, said clamping member having an inner surface, an outer surface and at least two apertures including a first aperture through which the securing rod passes and a second aperture for attachment of the clamping member to said flexible shaft;
   the flexible shaft comprising a locking collar mounted for sliding, linear movement at said second end for quick release connection to the device, said locking collar having at least one detent element for releasable engagement with the device.

8. A clamping apparatus as set forth in claim 7 in combination with a mounting stud adapted to be mounted on the device, the mounting stud including a locking recess adapted to accept the at least one detent element.

* * * * *